US010704043B2

(12) United States Patent
Daniel et al.

(10) Patent No.: US 10,704,043 B2
(45) Date of Patent: Jul. 7, 2020

(54) NUCLEIC ACID NANOSTRUCTURES WITH CORE MOTIFS

(71) Applicant: Exicure, Inc., Skokie, IL (US)

(72) Inventors: Weston Daniel, Evanston, IL (US); Scott Mix, Chicago, IL (US)

(73) Assignee: Exicure, Inc., Skokie, IL (US)

( * ) Notice: Subject to any disclaimer, the term of this patent is extended or adjusted under 35 U.S.C. 154(b) by 0 days.

(21) Appl. No.: 15/543,728

(22) PCT Filed: Jan. 14, 2016

(86) PCT No.: PCT/US2016/013365
§ 371 (c)(1),
(2) Date: Jul. 14, 2017

(87) PCT Pub. No.: WO2016/115320
PCT Pub. Date: Jul. 21, 2016

(65) Prior Publication Data
US 2018/0327741 A1 Nov. 15, 2018

Related U.S. Application Data

(60) Provisional application No. 62/103,303, filed on Jan. 14, 2015.

(51) Int. Cl.
| C12N 15/113 | (2010.01) |
| C12N 15/88 | (2006.01) |
| A61K 47/54 | (2017.01) |
| C12N 15/11 | (2006.01) |
| C12N 15/87 | (2006.01) |
| A61K 47/69 | (2017.01) |
| A61K 9/14 | (2006.01) |

(52) U.S. Cl.
CPC .......... *C12N 15/113* (2013.01); *A61K 47/544* (2017.08); *A61K 47/6911* (2017.08); *C12N 15/111* (2013.01); *C12N 15/87* (2013.01); *C12N 15/88* (2013.01); *A61K 9/143* (2013.01); *A61K 9/146* (2013.01); *C12N 15/1138* (2013.01); *C12N 2310/11* (2013.01); *C12N 2310/315* (2013.01); *C12N 2310/3183* (2013.01); *C12N 2310/341* (2013.01); *C12N 2310/3515* (2013.01); *C12N 2320/32* (2013.01)

(58) Field of Classification Search
CPC .............. C12N 15/113; C12N 2310/32; A61K 47/6911
See application file for complete search history.

(56) References Cited

U.S. PATENT DOCUMENTS

| 6,080,580 A * | 6/2000 | Baker ................ C12N 15/1136 435/366 |
| 8,431,544 B1 | 4/2013 | Agrawal et al. |
| 10,182,988 B2 | 1/2019 | Mirkin et al. |
| 10,208,310 B2 * | 2/2019 | Mader ..................... C07H 21/00 |
| 10,434,064 B2 | 10/2019 | Radovic-Moreno et al. |
| 2002/0156033 A1 | 10/2002 | Bratzler et al. |
| 2003/0022848 A1 * | 1/2003 | Baker ................ C12N 15/1136 514/44 R |
| 2003/0147966 A1 | 8/2003 | Franzen et al. |
| 2004/0014956 A1 * | 1/2004 | Woolf .................. A61K 31/713 536/23.1 |
| 2007/0148251 A1 | 6/2007 | Hossainy et al. |
| 2007/0218501 A1 | 9/2007 | Fogelman et al. |
| 2009/0209629 A1 | 8/2009 | Mirkin et al. |
| 2009/0317802 A1 | 12/2009 | Bhatia et al. |
| 2009/0322327 A1 | 12/2009 | Gao |
| 2010/0003317 A1 | 1/2010 | Akinc et al. |
| 2010/0111968 A1 * | 5/2010 | Branigan ............. C07K 16/244 514/1.1 |
| 2011/0305734 A1 | 12/2011 | Edelson et al. |
| 2013/0101512 A1 | 4/2013 | Mirkin et al. |
| 2013/0123333 A1 | 5/2013 | Mirkin et al. |
| 2013/0295129 A1 * | 11/2013 | Irvine ................ A61K 39/0005 424/194.1 |
| 2015/0086985 A1 | 3/2015 | Giljohann et al. |
| 2016/0186178 A1 | 6/2016 | Radovic-Moreno et al. |
| 2016/0194642 A1 * | 7/2016 | Gryaznov .............. A61K 39/39 424/193.1 |
| 2016/0310425 A1 * | 10/2016 | Mirkin .................... A61K 9/127 |
| 2017/0175121 A1 | 6/2017 | Gryaznov |
| 2017/0240960 A1 | 8/2017 | Giljohann et al. |
| 2018/0042848 A1 | 2/2018 | Gryaznov et al. |
| 2018/0214376 A1 | 8/2018 | Giljohann |
| 2018/0320184 A1 | 11/2018 | Radovic-Moreno et al. |
| 2018/0327741 A1 | 11/2018 | Daniel et al. |
| 2019/0142739 A1 | 5/2019 | Patel et al. |

(Continued)

FOREIGN PATENT DOCUMENTS

| WO | WO 97/48715 A1 | 12/1997 |
| WO | WO 2005/063288 A1 | 7/2005 |

(Continued)

OTHER PUBLICATIONS

Banga et al. Journal of the American Chemical Society 136, 9866-9869 (Year: 2014).*
Choi et al. PNAS 110 7625-7630 (Year: 2013).*
Andrews et al., Conjugation of Lipid and CpG-Containing Oligonucleotide Yields an Efficient Method for Liposome Incorporation. Bioconjuqate Chem. 2011;22:1279-1286.
Aurasense Therapeutics, NIH grant. Topically-delivered Target Gene Suppression of Immune Activation in Psoriasis. David Giljohann. Accessed on Aug. 2, 2017 from http://grantome.com/grant/NIH/R41-AR066438-01. Accessible online on Feb. 21, 2016 as as verified through Wayback Machine.
Baldwin, The NF-kappa B and I kappa B proteins: new discoveries and insights. Annu Rev Immunol. 1996;14:649-83.

(Continued)

*Primary Examiner* — Brian Whiteman
(74) *Attorney, Agent, or Firm* — Wolf, Greenfield & Sacks, P.C.

(57) ABSTRACT

Optimized inhibitory nucleic acids are provided. The nucleic acids have sequences which include an optimal inhibitory motif, such as a GGG. Related methods are also described.

20 Claims, 1 Drawing Sheet

Specification includes a Sequence Listing.

(56) References Cited

U.S. PATENT DOCUMENTS

| | | |
|---|---|---|
| 2019/0211338 A1 | 7/2019 | Mader et al. |
| 2019/0225968 A1 | 7/2019 | Anderson et al. |

FOREIGN PATENT DOCUMENTS

| | | | |
|---|---|---|---|
| WO | WO 2006/088833 A2 | 8/2006 | |
| WO | WO 2006/138145 A1 | 12/2006 | |
| WO | WO-2009051451 A2 * | 4/2009 | ........... A61K 9/1275 |
| WO | WO 2009/061515 A1 | 5/2009 | |
| WO | WO 2009/120887 A2 | 10/2009 | |
| WO | WO 2010/105209 A1 | 9/2010 | |
| WO | WO 2011/143608 A1 | 11/2011 | |
| WO | WO 2013/098813 A1 | 7/2013 | |
| WO | WO 2013/177419 A1 | 11/2013 | |
| WO | WO 2014/025795 A1 | 2/2014 | |
| WO | WO 2014/088830 A1 | 6/2014 | |
| WO | WO 2014/123935 A2 | 8/2014 | |
| WO | WO 2014/133547 A1 | 9/2014 | |
| WO | WO 2014/175836 A1 | 10/2014 | |
| WO | WO 2015/153975 A1 | 10/2015 | |
| WO | WO 2015/187966 A1 | 12/2015 | |
| WO | WO 2016/149323 A2 | 9/2016 | |
| WO | WO 2019/168558 A2 | 9/2019 | |
| WO | WO 2019/169203 A2 | 9/2019 | |
| WO | WO 2019/246409 A2 | 12/2019 | |

OTHER PUBLICATIONS

Bunge et al., Lipophilic oligonucleotides spontaneously insert into lipid membranes, bind complementary DNA strands, and sequester into lipid-disordered domains. Langmuir. Apr. 10, 2007;23(8):4455-64. Epub 2007 ar 17.
Burgess, Liposome preparation—Avanti® Polar Lipids. Sigma-Aldrich. 1998. 3 pages.
Cho et al., Targeted delivery of siRNA-generating DNA nanocassettes using multifunctional nanoparticles. Small. Jun. 10, 2013;9(11):1964-73. doi: 10.1002/smll.201201973. Epub Jan. 6, 2013.
Cutler et al., Spherical nucleic acids. J Am Chem Soc. Jan 25, 2012;134(3):1376-91. doi: 10.1021/ja209351u. Epub Jan. 9, 2012.
Dikmen et al., Targeting critical steps of cancer metastasis and recurrence using telomerase template antagonists. Biochim Biophys Acta. Apr. 2009;1792(4):240-7. doi: 10.1016/j.bbadis.2009.01.018. Epub Feb. 9, 2009.
Extended European Search Report dated Jun. 8, 2018 in connection with EP Application No. 16737865.2.
Genbank Submission; NIH/NCBI, Accession No. NM_014339.6. Tang et al., May 5, 2014. 8 pages.
Giljohann et al., Gene regulation with polyvalent siRNA-nanoparticle conjugates. J Am Chem Soc. Feb. 18, 2009;131(6):2072-3.
Grijalvo et al., Oligonucleotide delivery: a patent review (2010-2013). Expert Opin Ther Pat. Jul. 2014;24(7):801-19. doi:10.1517/13543776.2014.915944. Epub May 5, 2014.
Gissot et al., Nucleoside, nucleotide and oligonucleotide based amphiphiles: a successful marriage of nucleic acids with lipids. Org. Biomol. Chem. 2008;6:1324-33.
International Preliminary Report on Patentability dated Jul. 27, 2017 in connection wtih PCT/US2016/013365.
International Search Report and Written Opinion dated May 16, 2016 in connection with PCT/US2016/013365.
Ivanov et al., Interleukin-17 as a drug target in human disease. Trends Pharmacol Sci. Feb. 2009;30(2):95-103. doi: 10.1016/j.tips.2008.11.004. Epub Jan. 21, 2009.
Jensen et al., Spherical nucleic acid nanoparticle conjugates as an RNAi-based therapy for glioblastoma, Sci. Trans. Med., 5:209ra152 (2013).
Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.
Körner et al., Mammalian tyrosinase catalyzes three reactions in the biosynthesis of melanin. Science. Sep. 17, 1982;217(4565):1163-5.
Lewandowski et al., Topically delivered spherical nucleic acid nanoconjugates targeting TNF improve the psoriatic phenotype. J Invest Dermatol. 2015 135:S71. Abstract 413.
Li et al., "Molecular spherical nucleic acids," PNAS pp. 1-5 (2018).
Neeper et al., Cloning and expression of a cell surface receptor for advanced glycosylation end products of proteins. J Biol Chem. Jul. 25, 1992;267(21):14998-5004.
No Author Listed Spacer 18 (Hexathylene glycol) Oligonucleotide Modification. BioSynthesis. Last accessed Nov. 7, 2019 via https://www.biosyn.com/oligonucleotideproduct/spacer-18-heg-oligonucleotide-modification.aspx. 3 pages.
No Author Listed Spacer 18 (hexathyleneglycol) GeneLink. Last accessed Nov. 7, 2019 via http://genelink.com/newsite/products/mod_detail.asp?modid=19. 2 pages.
Patel et al., Scavenger receptors mediate cellular uptake of polyvalent oligonucleotide-functionalized gold nanoparticles, Bioconj. Chem., 21:2250 (2010).
Peter et al., Characterization of suppressive oligodeoxynucleotides that inhibit Toll-like receptor-9-mediated activation of innate immunity. Immunology. Jan. 2008;123(1):118-28. Epub Oct. 23, 2007.
Pfeiffer et al., Bivalent Cholesterol-Based Coupling of Oligonucleotides to Lipid Membrane Assemblies. J. Am. Chem. Soc. 2004;126:10224-10225.
Phan, Human telomeric G-quadruplex: structures of DNA and RNA sequences. FEBS J. Mar. 2010;277(5):1107-17. doi: 10.1111/j.1742-4658.2009.07464.x. Epub 2009; Nov. 27.
Polizzi et al., Water-soluble nitric oxide-releasing gold nanoparticles. Langmuir. Apr. 24, 2007;23(9):4938-43. Epub Mar. 22, 2007.
Prasad et al., Oligonucleotides tethered to a short polyguanylic acid stretch are targeted to macrophages: enhanced antiviral activity of a vesicular stomatitis virus-specific antisense oligonucleotide. Antimicrob Agents Chemother. Nov. 1999;43(11):2689-96.
Radovic-Moreno et al., Immunomodulatory spherical nucleic acids. Proc Natl Acad Sci U S A Mar. 31, 2015;112(13):3892-7. doi: 10.1073/pnas.1502850112. Epub Mar. 16, 2015.
Rothrock et al., Synthesis of nitric oxide-releasing gold nanoparticles. J Am Chem Soc. Jul. 6, 2005;127(26):9362-3.
Thaxton et al., Templated Spherical High Density Lipoprotein Nanoparticles, J. Am. Chem. Soc., 2009, 131 (4), 1384-1385.
Vorobjev et al., Nuclease resistance and RNase H sensitivity of oligonucleotides bridged by oligomethylenediol and oligoethylene glycol linkers. Antisense Nucleic Acid Drug Dev. Apr. 2001;11(2):77-85.
Wilton et al. Antisense oligonucleotide-induced exon skipping across the human dystrophin gene transcript. Mol Ther. Jul. 2007;15(7):1288-96. Epub Feb. 6, 2007.
Wolfe et al., Modulation of Tetraplex Formation by Chemical Modifications of a G4-Containing Phosphorothioate Oligonucleotide. J. Am. Chem. Soc. 1996, 118, 6301-6302 (Year: 1996).
Wu et al., DNA aptamer-micelle as an efficient detection/delivery vehicle toward cancer cells. Proc Natl Acad Sci U S A. Jan. 5, 2010;107(1):5-10. doi: 10.1073/pnas.0909611107. Epub Dec. 22, 2009.
Xie et al., Interleukin (IL)-22, a novel human cytokine that signals through the interferon receptor-related proteins CRF2-4 and IL-22R. J Biol Chem. Oct. 6, 2000;275(40):31335-9.
Young et al., Hollow spherical nucleic acids for intracellular gene regulation based upon biocompatible silica shells, Nano Lett., 12:3867 (2012).
Zheng et al., A spherical nucleic acid platform based on self-assembled DNA biopolymer for high-performance cancer therapy. ACS Nano. Aug. 27, 2013;7(8):6545-54. doi: n402344v. Epub Jul. 23, 2013.
Zheng et al., Topical delivery of siRNA-based spherical nucleic acid nanoparticle conjugates for gene regulation. Proc Natl Acad Sci U S A Jul. 24, 2012;109(30):11975-80. doi: 10.1073/pnas.1118425109. Epub Jul. 6, 2012.

* cited by examiner

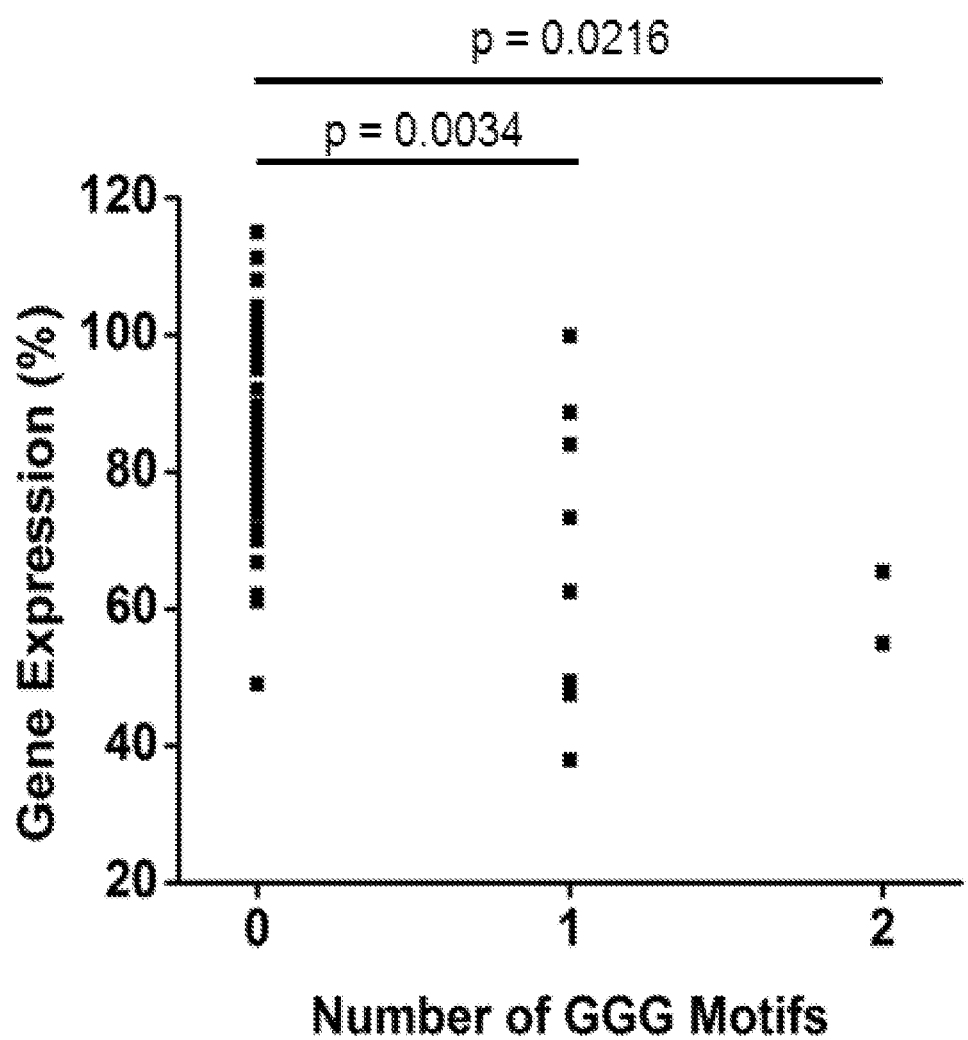

SEQUENCE LISTING

<160> NUMBER OF SEQ ID NOS: 82

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
actctggcgc agaaattagg          20

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
tgtagcccat ttgtctcagg          20

<210> SEQ ID NO 3
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:

```
<221> NAME/KEY: misc_feature
<222> LOCATION: (1)..(1)
<223> OTHER INFORMATION: Modified with /FAM/
<220> FEATURE:
<221> NAME/KEY: misc_feature
<222> LOCATION: (25)..(25)
<223> OTHER INFORMATION: Modified with /BHQ1/

<400> SEQUENCE: 3
acaactatga ggtctctggg ggtac                                              25

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
gctgctgacc atcttgactg                                                    20

<210> SEQ ID NO 5
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 5
ggactggaat ttcacgtgct g                                                  21

<210> SEQ ID NO 6
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified with /FAM/
<220> FEATURE:
<221> NAME/KEY: misc_feature
<222> LOCATION: (22)..(22)
<223> OTHER INFORMATION: Modified with /BHQ1/

<400> SEQUENCE: 6
ctgaggaccc ctcggatctg ct                                                 22

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
agaaatgcca gacactccag                                                    20

<210> SEQ ID NO 8
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 8
gatggagatg cccgtgatg                                                     19
```

```
<210> SEQ ID NO 9
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified with /FAM/
<220> FEATURE:
<221> NAME/KEY: misc_feature
<222> LOCATION: (23)..(23)
<223> OTHER INFORMATION: Modified with /BHQ1/

<400> SEQUENCE: 9
ccaattccgg actacatgcc cct                                           23

<210> SEQ ID NO 10
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 10
gtcatcttgt ggcaaaggc                                                19

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
tgattcagtt ctgcacgctc                                               20

<210> SEQ ID NO 12
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified with /FAM/
<220> FEATURE:
<221> NAME/KEY: misc_feature
<222> LOCATION: (25)..(25)
<223> OTHER INFORMATION: Modified with /BHQ1/

<400> SEQUENCE: 12
caacgccgag gagaggagag gaagg                                         25

<210> SEQ ID NO 13
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 13
tcctaactta ctcagcccag catc                                          24

<210> SEQ ID NO 14
```

```
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 14
tggctgttgt actcctccaa tcg                                          23

<210> SEQ ID NO 15
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified with /FAM/
<220> FEATURE:
<221> NAME/KEY: misc_feature
<222> LOCATION: (29)..(29)
<223> OTHER INFORMATION: Modified with /BHQ1/

<400> SEQUENCE: 15
tctcctcttg gcagattgtc tgtagccga                                    29

<210> SEQ ID NO 16
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 16
caaggtcatc catgacaact ttg                                          23

<210> SEQ ID NO 17
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 17
gggccatcca cagtcttct                                               19

<210> SEQ ID NO 18
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified with /HEX/
<220> FEATURE:
<221> NAME/KEY: misc_feature
<222> LOCATION: (25)..(25)
<223> OTHER INFORMATION: Modified with /BHQ1/

<400> SEQUENCE: 18
accacagtcc atgccatcac tgcca                                        25

<210> SEQ ID NO 19
<211> LENGTH: 18
<212> TYPE: DNA
<213> ORGANISM: Artificial Sequence
```

```
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (7)..(13)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Chol/

<400> SEQUENCE: 19
agguggcttg aggguagu                                                  18

<210> SEQ ID NO 20
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (7)..(13)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 20
agguggcttg aggguagu                                                  18

<210> SEQ ID NO 21
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (18)..(18)
<223> OTHER INFORMATION: Modified with /isp18//isp18//Chol/

<400> SEQUENCE: 21
tagagtgagg tcaggctt                                                  18

<210> SEQ ID NO 22
<211> LENGTH: 20
<212> TYPE: DNA
<213> ORGANISM: Artificial Sequence
```

<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 22
uuagagtgag gtcaggcuuu                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 23
guucctcatt accaaauagc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 24

```
guucctcatt accaaauagc                                                20

<210> SEQ ID NO 25
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 25
cugagtgaaa acagcaagac                                                20

<210> SEQ ID NO 26
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (7)..(13)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 26
cucugcctga aagcuggc                                                  18

<210> SEQ ID NO 27
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
```

-continued

```
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 27
ucauggtttc caggauuacg                                            20

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 28
gagcactggc aggtccuauu                                            20

<210> SEQ ID NO 29
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 29
uuccucatta ccaaauag                                              18

<210> SEQ ID NO 30
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
```

```
<223> OTHER INFORMATION: Modified with 2' O-Methyl
<220> FEATURE:
<221> NAME/KEY: misc_feature
<222> LOCATION: (1)..(21)
<223> OTHER INFORMATION: Modified with phosphorothioate internucleotide
      linkage
<220> FEATURE:
<221> NAME/KEY: misc_feature
<222> LOCATION: (16)..(21)
<223> OTHER INFORMATION: Modified with 2' O-Methyl
<220> FEATURE:
<221> NAME/KEY: misc_feature
<222> LOCATION: (21)..(21)
<223> OTHER INFORMATION: Modified with /iSp18//iSp18//Stearyl/

<400> SEQUENCE: 30
gugcugaccu cccauguacu c                                             21

<210> SEQ ID NO 31
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 31
acacaggctc tagggaaa                                                 18

<210> SEQ ID NO 32
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (7)..(13)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 32
caugguuucc aggauuac                                                 18

<210> SEQ ID NO 33
```

```
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (7)..(13)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 33
uuggaagaag gcuacacu                                                 18

<210> SEQ ID NO 34
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 34
ccucugccug aaagcuggcc                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
```

<223> OTHER INFORMATION: Modified with /iSp18//iSp18//Stearyl/

<400> SEQUENCE: 35
ggcugagtaa gttaggauuu                                                20

<210> SEQ ID NO 36
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 36
cactagtttc caagtcagat                                                20

<210> SEQ ID NO 37
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 37
cacgctgagg tccatctc                                                  18

<210> SEQ ID NO 38
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(19)
<223> OTHER INFORMATION: Modified with phosphorothioate internucleotide
      linkage
<220> FEATURE:
<221> NAME/KEY: misc_feature
<222> LOCATION: (19)..(19)
<223> OTHER INFORMATION: Modified with /iSp18//iSp18//Stearyl/

<400> SEQUENCE: 38
caactgctgt tccggctgc                                                 19

<210> SEQ ID NO 39
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)

```
<223> OTHER INFORMATION: Modified with phosphorothioate internucleotide
      linkage
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 39
ccacgctgag gtccatctcc                                                   20

<210> SEQ ID NO 40
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 40
tgccaggtgg cgaccgtg                                                     18

<210> SEQ ID NO 41
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 41
aactgctgtt ccggctgc                                                     18

<210> SEQ ID NO 42
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 42
atgctgacag cacggctttc                                                   20

<210> SEQ ID NO 43
<211> LENGTH: 20
<212> TYPE: DNA
<213> ORGANISM: Artificial Sequence
```

```
<220> FEATURE:
<223> OTHER INFORMATION: Synthetic Polynucleotide
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 43
ctcctttcca ttcctgttca                                                 20

<210> SEQ ID NO 44
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 44
cacuagtttc caagtcagau                                                 20

<210> SEQ ID NO 45
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 45
augccaggtg gcgaccguga                                                 20

<210> SEQ ID NO 46
<211> LENGTH: 18
<212> TYPE: DNA
<213> ORGANISM: Artificial Sequence
```

<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 46
acuaguttcc aagucaga                                                       18

<210> SEQ ID NO 47
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 47
ugccaggtgg cgaccgug                                                       18

<210> SEQ ID NO 48
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (1)..(19)
<223> OTHER INFORMATION: Modified with phosphorothioate internucleotide
      linkage
<220> FEATURE:
<221> NAME/KEY: misc_feature
<222> LOCATION: (14)..(19)
<223> OTHER INFORMATION: Modified with 2' O-Methyl
<220> FEATURE:
<221> NAME/KEY: misc_feature
<222> LOCATION: (19)..(19)
<223> OTHER INFORMATION: Modified with /iSp18//iSp18//Stearyl/

<400> SEQUENCE: 48
caacugcugu uccggcugc                                              19

<210> SEQ ID NO 49
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 49
atgccaggtg gcgaccgtga                                             20

<210> SEQ ID NO 50
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 50
cugcuuccuu ccaggguc                                               18

<210> SEQ ID NO 51
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 51

```
cuucccucca aggugcau                                                   18

<210> SEQ ID NO 52
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 52
cccacugcac agucaggg                                                   18

<210> SEQ ID NO 53
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 53
aggcaguugc ccuggcug                                                   18

<210> SEQ ID NO 54
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 54
```
tcctgcagag aaaggccacc                                               20

<210> SEQ ID NO 55
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 55
cttccctcca aggtgcat                                                 18

<210> SEQ ID NO 56
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 56
aggctatgcc gctgtgga                                                 18

<210> SEQ ID NO 57
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 57
uagggcgtgt gtgggucugu                                               20

<210> SEQ ID NO 58
<211> LENGTH: 20
<212> TYPE: DNA
<213> ORGANISM: Artificial Sequence

```
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 58
cucactccac tcaccuccca                                                    20

<210> SEQ ID NO 59
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 59
ugucctgttt gctctccugu                                                    20

<210> SEQ ID NO 60
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 60
```
agacgauaac cagaccgcug                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 61
uaacucugca cccucgaggu                                               20

<210> SEQ ID NO 62
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 62
tgtcctgttt gctctcctgt                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 63
uugucatcac ttttgucaca                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (1)..(20)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 64
ccacgctgag gtccaucucc                                              20

<210> SEQ ID NO 65
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (1)..(18)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 65
ugucugtgca aaucccca                                                18

<210> SEQ ID NO 66
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature

```
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 66
uagggcgtgt gtgggucugu                                           20

<210> SEQ ID NO 67
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 67
ccacatagta ggtgcacaau                                           20

<210> SEQ ID NO 68
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 68
cucactccac tcaccuccca                                           20

<210> SEQ ID NO 69
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
```

-continued

<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 69
ugucctgttt gctctccugu                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 70
agacgataac cagaccgcug                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 71
uaacuctgca ccctcgaggu                                              20

<210> SEQ ID NO 72

```
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (7)..(13)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 72
acuaguuucc aagucaga                                                 18

<210> SEQ ID NO 73
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (7)..(13)
<223> OTHER INFORMATION: Modified with phosphorothioate internucleotide
      linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 73
cugcuuccuu ccaggguc                                                 18

<210> SEQ ID NO 74
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
```

<223> OTHER INFORMATION: Modified with /iSp18//iSp18//Stearyl/

<400> SEQUENCE: 74
ucccactgca cagtcagggc                                              20

<210> SEQ ID NO 75
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 75
caggcagttg ccctggcugg                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
      linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 76
cucccttggc ctctacucug                                              20

<210> SEQ ID NO 77
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (7)..(13)
<223> OTHER INFORMATION: Modified with phosphorothioate internucleotide

```
        linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 77
ugucugtgca aaucccca                                                18

<210> SEQ ID NO 78
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (7)..(13)
<223> OTHER INFORMATION: Modified with phosphorothioate internucleotide
        linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 78
aggcagttgc ccuggcug                                                18

<210> SEQ ID NO 79
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(18)
<223> OTHER INFORMATION: Modified with phosphorothioate internucleotide
        linkage
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 79
aggcagttgc cctggctg                                                18

<210> SEQ ID NO 80
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: Modified with 2' O-Methyl
<220> FEATURE:
<221> NAME/KEY: misc_feature
<222> LOCATION: (6)..(16)
<223> OTHER INFORMATION: Modified with phosphorothioate internucleotide
```

```
            linkage
<220> FEATURE:
<221> NAME/KEY: misc_feature
<222> LOCATION: (16)..(20)
<223> OTHER INFORMATION: Modified with 2' O-Methyl
<220> FEATURE:
<221> NAME/KEY: misc_feature
<222> LOCATION: (20)..(20)
<223> OTHER INFORMATION: Modified with /iSp18//iSp18//Stearyl/

<400> SEQUENCE: 80
ugguaatggg tagatucguu                                              20

<210> SEQ ID NO 81
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (7)..(13)
<223> OTHER INFORMATION: Modified with phosphorothioate internucleotide
            linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Stearyl/

<400> SEQUENCE: 81
guuucaccac ccaauucc                                                18

<210> SEQ ID NO 82
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: Modified with 2' O-Methyl
<220> FEATURE:
<221> NAME/KEY: misc_feature
<222> LOCATION: (7)..(13)
<223> OTHER INFORMATION: Modified with phosphorothioate internucleotide
            linkage
<220> FEATURE:
<221> NAME/KEY: misc_feature
<222> LOCATION: (13)..(18)
<223> OTHER INFORMATION: Modified with 2' O-Methyl
<220> FEATURE:
<221> NAME/KEY: misc_feature
<222> LOCATION: (18)..(18)
<223> OTHER INFORMATION: Modified with /iSp18//iSp18//Chol/

<400> SEQUENCE: 82
guuucaccac ccaauucc                                                18
```

NUCLEIC ACID NANOSTRUCTURES WITH CORE MOTIFS

RELATED APPLICATIONS

This application is a national stage filing under 35 U.S.C. § 371 of PCT International Application PCT/US2016/013365, filed on Jan. 14, 2016, which claims priority under 35 U.S.C. § 119(e) to U.S. Provisional Application Ser. No. 62/103,303, entitled "NUCLEIC ACID NANOSTRUCTURES WITH CORE MOTIFS" filed on Jan. 14, 2015, which are herein incorporated by reference in their entirety.

BACKGROUND OF THE INVENTION

Inhibitory nucleic acids downregulate gene expression through a variety of mechanisms. Antisense oligonucleotides, for instance, are typically single strands of DNA or RNA that are at least partially complementary to a chosen target sequence and function by preventing protein translation of specific messenger RNA strands. Double-stranded RNA (dsRNA) is another type of inhibitory nucleic acid that can induce sequence-specific posttranscriptional gene silencing in many organisms by a process known as RNA interference (RNAi). These functional RNAs include at least two types of small RNA molecules (1) siRNA molecules that induce mRNA degradation, and (2) miRNAs (microRNAs) that induce translational inhibition. Other small RNAs work at the transcriptional level by affecting DNA and histone methylation.

SUMMARY OF THE INVENTION

In some aspects the invention is a spherical nucleic acid (SNA) having a dense configuration of oligonucleotides radially positioned around a lipidated structure, wherein the oligonucleotides have a length of 8-200 nucleotides and include at least one GGG.

In some embodiments the oligonucleotides have the following structure: 5' $X_1GGGX_2$ 3' wherein $X_1$ and $X_2$ are independently of one another any nucleotide and optionally wherein $X_1$ is selected from the group consisting of G and A. In other embodiments 5' $X_1GGGX_2$ 3' is selected from the group consisting of GGGG, GGGT, AGGG and GGGC. In other embodiments the at least one GGG is positioned at the 5' end of the oligonucleotide within the first 10 nucleotides. In yet other embodiments at least one GGG is positioned at the 3' end of the oligonucleotide within the 10 nucleotides at the 3' end or the at least one GGG is positioned in the center of the oligonucleotide. In other embodiments the oligonucleotides include 2-5 GGG motifs.

In another embodiment the oligonucleotides comprise 2-10,000 oligonucleotides. In other embodiments the oligonucleotides comprise 100-10,000, 500-10,000, 1,000-10,000, 5,000-10,000, 6,000-10,000, 7,000-10,000, 8,000-10,000, 9,000-10,000 or 9,500-10,000 oligonucleotides.

The SNA in some embodiments is not a dendrimer.

In some embodiments the oligonucleotides are antisense oligonucleotides. In other embodiments the oligonucleotides are nucleolipids. In yet other embodiments the oligonucleotides are siRNAs.

In some embodiments the oligonucleotides are comprised of single-stranded or double-stranded DNA oligonucleotides. In other embodiments the oligonucleotides are comprised of single-stranded or double-stranded RNA oligonucleotides. In other embodiments the oligonucleotides are comprised of chimeric RNA-DNA oligonucleotides. In another embodiment the oligonucleotides are comprised of RNA-DNA or DNA-RNA oligonucleotide heteroduplexes. In another embodiment the oligonucleotides are comprised of combinations of single-stranded or double-stranded DNA, RNA, or chimeric RNA-DNA oligonucleotides. In some embodiments the oligonucleotides are double stranded and do not have an overhang. In other embodiments the oligonucleotides are linear.

In another embodiment the oligonucleotides have structurally and nucleotide sequence identical oligonucleotides. In some embodiments the oligonucleotides have at least two structurally and nucleotide sequence different oligonucleotides.

In other embodiments the oligonucleotides have 2-10 different nucleotide sequences.

In an embodiment at least one of the oligonucleotides is a modified oligonucleotide. In some embodiments at least 50% of the oligonucleotides are modified oligonucleotides. In yet other embodiments all of the oligonucleotides are modified oligonucleotides. In some embodiments the oligonucleotides have at least one phosphorothioate linkage. In other embodiments the oligonucleotides do not have a phosphorothioate linkage.

In another embodiment the nanostructure comprises a liposomal core having a lipid bilayer.

In some embodiments at least one oligonucleotide has its 5'-terminus exposed to the outside surface of the nanostructure. In other embodiments all of the oligonucleotides have their 5'-terminus exposed to the outside surface of the nanostructure. In other embodiments at least one oligonucleotide has its 3'-terminus exposed to the outside surface of the nanostructure. All of the oligonucleotides have their 3'-terminus exposed to the outside surface of the nanostructure in other embodiments.

In another embodiment the oligonucleotides are directly linked to the core. In some embodiments the oligonucleotides are indirectly linked to the core through a linker.

In other embodiments the oligonucleotides are indirectly linked to the core through more than one linker.

In other embodiments the oligonucleotides are reversibly or irreversibly coupled to the core.

In some embodiments the oligonucleotides are linked to the core through a linker. The linker in some embodiments is a chemical structure containing one or more thiol groups, including various chain length alkane thiols, cyclic dithiol, lipoic acid, PEG-thiol, and other thiol group containing linkers. Optionally the oligonucleotides are linked to a liposomal core and the linker is one or more of the following linkers: tocopherols, sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states and derivatives thereof.

The core in some embodiments is a solid or hollow core and may be inert, paramagnetic or supramagnetic. In embodiments the solid core is comprised of noble metals, including gold and silver, transition metals including iron and cobalt, metal oxides including silica, polymers or combinations thereof. In other embodiments the core is a polymeric core and wherein the polymeric core is comprised of amphiphilic block copolymers, hydrophobic polymers including polystyrene, poly(lactic acid), poly(lactic co-glycolic acid), poly(glycolic acid), poly(caprolactone) and other biocompatible polymers.

In another embodiment the core is a liposomal core and is comprised of one type of lipid or alternatively is comprised of 2-10 different lipids. The liposomal core in some embodiments is comprised of one or more lipids selected from: sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, and derivatives thereof.

In another embodiment the SNA further comprises an active agent. In some embodiments the active agent is mixed together with the SNA. In other embodiments the active agent is linked directly to the oligonucleotide shell. In some embodiments the active agent is linked indirectly to the oligonucleotide shell through a linker. In other embodiments the active agent is linked directly to the core. In yet another embodiment the active agent is linked indirectly to the core through a linker. In another embodiment an active agent-oligonucleotide conjugate is linked to the core through oligonucleotide hybridization. In some embodiments the active agent is associated with the core by being embedded within the core, optionally the liposomal core. In some embodiments the active agent is encapsulated within the liposomal core in an inner aqueous layer.

In some embodiments the SNA is a self-assembling nanostructure.

A method for reducing gene expression by contacting a cell with a nanostructure comprising a nucleotide amphiphile having an inhibitory oligonucleotide having at least one GGG motif, wherein gene expression is reduced to a greater extent than when the cell is contacted with free inhibitory oligonucleotide is provided in other aspects of the invention. The nucleotide amphiphile may be a spherical nucleic acid (SNA), as described herein.

In some embodiments the inhibitory oligonucleotide is an antisense oligonucleotide. In other embodiments the inhibitory oligonucleotide has the following structure: 5' $X_1GGGX_2$ 3' wherein $X_1$ and $X_2$ are independently of one another any nucleotide, wherein $X_1$ optionally is selected from the group consisting of G and A. In some embodiments 5' $X_1GGGX_2$ 3' is selected from the group consisting of GGGG, GGGT, AGGG and GGGC.

In some embodiments the inhibitory oligonucleotide is complementary to a target sequence selected from the group consisting of TNF, Bcl-2, EGFR, mdm2, MyD88, PCSK9, survivin, VEGF, developmental genes (e.g. adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), oncogenes (e.g. ABLI, BLC1, BCL6, CBFA1, CBL, CSFIR, ERBA, ERBB, EBRB2, ETS1, ETS1, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES), tumor suppresser genes (e.g. APC, BRCA1, BRCA2, MADH4, MCC, NF1, NF2, RB1, TP53 and WT1), enzymes (e.g. ACP desaturases and hycroxylases, ADP-glucose pyrophorylases, ATPases, alcohol dehycrogenases, amylases, amyloglucosidases, catalases, cellulases, cyclooxygenases, decarboxylases, dextrinases, esterases, DNA and RNA polymerases, galactosidases, glucanases, glucose oxidases, GTPases, helicases, hemicellulases, integrases, invertases, isomersases, kinases, lactases, lipases, lipoxygenases, lysozymes, pectinesterases, peroxidases, phosphatases, phospholipases, phosphorylases, polygalacturonases, proteinases and peptideases, pullanases, recombinases, reverse transcriptases, topoisomerases, xylanases), and a TLR (e.g. TLR2, TLR3, TLR4, TLR5, TLR6, TLR7, TLR8 and TLR9).

The inhibitory oligonucleotide may be a therapeutic agent selected from the group consisting of anti-viral agents, anti-tumor agents, and agents for treating inherited disorders.

The method, in some embodiments, is a method for treating a disorder selected from the group consisting of an autoimmune disease, an infectious disease, transplant rejection or graft-versus-host disease, malignancy, a pulmonary disorder, an intestinal disorder, a cardiac disorder, sepsis, a spondyloarthropathy, a metabolic disorder, anemia, pain, a hepatic disorder, a skin disorder, a nail disorder, rheumatoid arthritis, psoriasis, psoriasis in combination with psoriatic arthritis, ulcerative colitis, Crohn's disease, vasculitis, Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriatic arthritis, and chronic plaque psoriasis.

In another aspect a composition for use in the treatment of disease comprises the SNA and embodiments thereof.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. The details of one or more embodiments of the invention are set forth in the accompanying Detailed Description, Examples, Claims, and FIGURES. Other features, objects, and advantages of the invention will be apparent from the description and from the claims.

BRIEF DESCRIPTION OF THE DRAWINGS

The accompanying drawings are not intended to be drawn to scale. In the drawings, each identical or nearly identical component that is illustrated in various FIGURES is represented by a like numeral. For purposes of clarity, not every component may be labeled in every drawing. In the drawings:

FIG. 1 is a graph depicting data that shows that the presence of a GGG motif in SNA-formulated oligonucleotides correlates with a greater gene knockdown in human keratinocytes. There are statistically significant differences between zero GGG motifs and both one motif (p=0.0034) and two motifs (p=0.0216).

DETAILED DESCRIPTION

Methods and products for inhibiting gene expression are provided herein. Optimal sequence motifs for inhibiting gene expression using inhibitory nucleic acids have been discovered herein. In particular it has been discovered that oligonucleotides including at least one GGG motif are more effective at reducing gene expression than similar oligonucleotides that lack the GGG motif.

The inhibitory oligonucleotides or inhibitory nucleic acids of the invention preferably have the following structure:

wherein $X_1$ and $X_2$ are independently of one another any nucleotide. In some embodiments $X_1$ is G, A or T. In other embodiments 5' $X_1GGGX_2$ 3' is selected from the group consisting of GGGG, GGGT, AGGG and GGGC.

The oligonucleotides may have a single GGG motif or multiple GGG motifs. In some instances the oligonucleotides include 2-10 GGG motifs and/or GGGG, GGGT, AGGG and GGGC GGGG, GGGT, AGGG or GGGC motifs in any combination.

The at least one GGG may be positioned anywhere in the oligonucleotide. For instance it may be positioned at the 5' end of the oligonucleotide within the first 10 nucleotides. Alternatively it may be positioned at the 3' end of the oligonucleotide within the 10 nucleotides at the 3' end. The at least one GGG may also be positioned in the center of the oligonucleotide.

An oligonucleotide, as used herein, refers to any nucleic acid containing molecule. The terms "oligonucleotide" and "nucleic acid" are used interchangeably to mean multiple nucleotides (i.e., molecules comprising a sugar (e.g., ribose or deoxyribose) linked to a phosphate group and to an exchangeable organic base, which is either a substituted pyrimidine (e.g., cytosine (C), thymidine (T) or uracil (U)) or a substituted purine (e.g., adenine (A) or guanine (G)). The terms shall also include oligonucleosides (i.e., a oligonucleotide minus the phosphate) and any other organic base containing polymer.

The nucleic acid may be DNA, RNA, PNA, LNA, ENA, nucleolipids or combinations or modifications thereof. It may also be single, double or triple stranded. Thus the oligonucleotide may be a wide variety of molecules including but not limited to: single-stranded deoxyribonucleotides, ribonucleotides, and other single-stranded oligonucleotides incorporating one or a multiplicity of modifications known to those skilled in the art, double-stranded deoxyribonucleotides, ribonucleotides, and other double-stranded oligonucleotides incorporating one or a multiplicity of modifications known to those skilled in the art.

The inhibitory oligonucleotides, also referred to herein as inhibitory nucleic acids, include but are not limited to antisense nucleic acids (single or double stranded), RNAi oligonucleotides, ribozymes, peptides, DNAzymes, peptide nucleic acids (PNAs), triple helix forming oligonucleotides, and aptamers and modified form(s) thereof directed to target sequences in genes, RNA transcripts, or proteins.

Antisense nucleic acids include modified or unmodified RNA, DNA, or mixed polymer nucleic acids, and primarily function by specifically binding to matching sequences resulting in modulation of peptide synthesis. Antisense nucleic acid binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm.

As used herein, the term "antisense nucleic acid" or "antisense oligonucleotide" describes a nucleic acid that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

Inhibitory oligonucleotides also include a broad range of RNAi-based modalities useful for inhibiting expression of a gene in a cell, such as siRNA-based oligonucleotides and/or altered siRNA-based oligonucleotides. Altered siRNA based oligonucleotides are those modified to alter potency, target affinity, safety profile and/or stability, for example, to render them resistant or partially resistant to intracellular degradation. Modifications, such as phosphorothioates, for example, can be made to oligonucleotides to increase resistance to nuclease degradation, binding affinity and/or uptake. In addition, modification of siRNAs at the 2'-sugar position and phosphodiester linkage confers improved serum stability without loss of efficacy.

Ribozymes have also been proposed as a means of both inhibiting gene expression of a mutant gene and of correcting the mutant by targeted trans-splicing. Ribozyme activity may be augmented by the use of, for example, non-specific nucleic acid binding proteins or facilitator oligonucleotides.

Multitarget ribozymes (connected or shotgun) have been suggested as a means of improving efficiency of ribozymes for gene suppression. Triple helix approaches have also been investigated for sequence-specific gene suppression. Triple helix forming oligonucleotides have been found in some cases to bind in a sequence-specific manner. Similarly, peptide nucleic acids have been shown to inhibit gene expression (Hanvey et al., Antisense Res. Dev. 1(4):307-17, 1991; Knudsen and Nielson Nucleic Acids Res. 24(3):494-500, 1996; Taylor et al., Arch. Surg. 132(11):1177-83, 1997). Minor-groove binding polyamides can bind in a sequence-specific manner to DNA targets and hence may represent useful small molecules for suppression at the DNA level. The diverse array of suppression strategies that can be employed includes the use of DNA and/or RNA aptamers that can be selected to target a protein of interest.

In some embodiments the inhibitory oligonucleotide is 100% identical to the nucleic acid target. In other embodiments it is at least 99%, 95%, 90%, 85%, 80%, 75%, 70%, or 50% identical to the nucleic acid target. The term "percent identical" refers to sequence identity between two nucleotide sequences. Percent identity can be determined by comparing a position in each sequence which may be aligned for purposes of comparison. Expression as a percentage of identity refers to a function of the number of identical amino acids or nucleic acids at positions shared by the compared sequences. Various alignment algorithms and/or programs may be used, including FASTA, BLAST, or ENTREZ-FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

An inhibitory oligonucleotide may be designed to have partial or complete complementarity with one or more target genes. Depending on the particular target gene, the nature of the inhibitory oligonucleotide and the level of expression of inhibitory oligonucleotide (e.g. depending on copy number, promoter strength) the procedure may provide partial or complete loss of function for the target gene. Quantitation of gene expression in a cell may show similar amounts of inhibition at the level of accumulation of target mRNA or translation of target protein.

"Inhibition of gene expression" refers to the absence or observable decrease in the level of protein and/or mRNA product from a target gene. "Specificity" refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). Depending on the assay, quantitation of the amount of gene expression allows one to determine a degree of inhibition which is greater than 10%, 33%, 50%, 90%, 95% or 99% as compared to a cell not treated according to the present invention. As an example, the efficiency of inhibition may be determined by assessing the amount of gene product in the cell.

In some instances the inhibitory oligonucleotide is a peptide nucleic acid (PNA). PNA oligomers have greater binding strength and specificity in the formation of a PNA/DNA duplex or PNA/DNA/PNA triplex as compared to a DNA/DNA duplex. PNAs also have increased stability to nucleases and proteases over a wide pH range, which makes them resistant to enzymatic degradation.

The oligonucleotides may be a duplex. As used herein, "duplex" includes a double-stranded nucleic acid molecule(s) in which complementary sequences or partially complementary sequences are hydrogen bonded to each other. The complementary sequences can include a sense strand and an antisense strand. A double-stranded oligonucleotide can be double-stranded over its entire length, meaning it has no overhanging single-stranded sequences and is thus blunt-ended. In other embodiments, the two strands of the double-stranded oligonucleotide can have different lengths producing one or more single-stranded overhangs. A double-stranded oligonucleotide of the invention can contain mismatches and/or loops or bulges. In some embodiments, it is double-stranded over at least about 70%, 80%, 90%, 95%, 96%, 97%, 98% or 99% of the length of the oligonucleotide. In some embodiments, the double-stranded oligonucleotide of the invention contains at least or up to 1, 2, 3, 4, 5, 6, 7, 8, 9, 10, 11, 12, 13, 14, or 15 mismatches.

Oligonucleotides associated with the invention can be modified such as at the sugar moiety, the phosphodiester linkage, and/or the base. As used herein, "sugar moieties" includes natural, unmodified sugars, including pentose, ribose and deoxyribose, modified sugars and sugar analogs. Modifications of sugar moieties can include replacement of a hydroxyl group with a halogen, a heteroatom, or an aliphatic group, and can include functionalization of the hydroxyl group as, for example, an ether, amine or thiol.

Modification of sugar moieties can include 2'-O-methyl nucleotides, which are referred to as "methylated." In some instances, oligonucleotides associated with the invention may only contain modified or unmodified sugar moieties, while in other instances, oligonucleotides contain some sugar moieties that are modified and some that are not.

In some instances, modified nucleomonomers include sugar- or backbone-modified ribonucleotides. Modified ribonucleotides can contain a non-naturally occurring base such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides can have the 2'-OH group replaced by an H, alkoxy (or OR), R or alkyl, halogen, SH, SR, amino (such as $NH_2$, $NHR$, $NR_2$), or CN group, wherein R is lower alkyl, alkenyl, or alkynyl. In some embodiments, modified ribonucleotides can have the phosphodiester group connecting to adjacent ribonucleotides replaced by a modified group, such as a phosphorothioate group.

In some aspects, 2'-O-methyl modifications can be beneficial for reducing undesirable cellular stress responses, such as the interferon response to double-stranded nucleic acids. Modified sugars can include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy (—OCH$_2$CH=CH$_2$), 2'-propargyl, 2'-propyl, ethynyl, ethenyl, propenyl, and cyano and the like. The sugar moiety can also be a hexose.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In some embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. The term "alkenyl" includes unsaturated aliphatic groups analogous in length and possible substitution to the alkyls described above, but that contain at least one double bond. Unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-N$^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", 2$^{nd}$ Ed., Wiley-Interscience, New York, 1999).

As used herein, the term "linkage" used in the context of an internucleotide linkage includes a naturally occurring, unmodified phosphodiester moiety (—O—(PO$^{2-}$)—O—) that covalently couples adjacent nucleomonomers. As used herein, the term "substitute linkage" or "modified linkage" or modified internucleotide linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothioate linkages.

In some aspects, oligonucleotides of the invention comprise 3' and 5' termini (except for circular oligonucleotides). The 3' and 5' termini of a oligonucleotide can be substantially protected from nucleases, for example, by modifying the 3' or 5' linkages (e.g., U.S. Pat. No. 5,849,902 and WO 98/13526). Oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl (CH$_2$—CH$_2$—CH$_3$), glycol (—O—CH$_2$—CH$_2$—O—) phosphate (PO$_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3' linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

In some aspects, oligonucleotides can be chimeric RNA-DNA oligonucleotides which include both DNA and RNA or DNA-RNA or RNA-DNA duplexes.

The oligonucleotides are preferably in the range of 2 to 1000, 2-500, 2-100, 5-500, 5-100, 10-500, 10-100, 8-100, 8-200, 10-50, 15-500, 15-100, 15-50, 20-500, 20-100, 20-50, or 20-40 bases or nucleotides in length. However, nucleic acids of other sizes are useful.

In some embodiments the oligonucleotides have a modified backbone such as a phosphorothioate (PS) backbone. In other embodiments the oligonucleotides have a phosphodiester (PO) backbone. In yet other embodiments oligonucleotides have a mixed or chimeric PO and PS backbone.

The inhibitory nucleic acids of the invention may be formulated as a nanostructure. The nanostructure typically is a spherical nucleic acid (SNA). An SNA, as used herein, refers to a dense configuration of oligonucleotides radially positioned around a lipidated structure. In some aspects, the invention is an SNA which is composed of a dense configuration of oligonucleotides radially positioned around a lipidated structure, wherein the oligonucleotides have a length of 8-200 nucleotides and include at least one GGG.

A lipidated structure is a spherical structure composed at least partially of lipids. In some instances the lipidated structure is composed entirely of lipids. The lipids may be arranged, for instance, in a lipid monolayer or a lipid bilayer. The lipids may be arranged around a hollow center, and thus form a hollow core. Alternatively the lipids may be arranged around a non-lipid material that forms a core. The core may be hollow or solid (including porous cores). A hollow core may be, for instance, an empty space surrounded by lipids i.e. a liposomal core or a hollow space surrounded by a non-lipid material. A solid core is a spherical shaped material that does not have a hollow center. Solid cores include porous or other materials having one or more breaks therein.

The term spherical as used herein refers to a general shape and does not imply or is not limited to a perfect sphere or round shape. It may include imperfections.

Solid cores can be constructed from a wide variety of materials known to those skilled in the art including but not limited to: noble metals (gold, silver), transition metals (iron, cobalt) and metal oxides (silica). In addition, these cores may be inert, paramagnetic, or supramagnetic. These solid cores can be constructed from either pure compositions of described materials, or in combinations of mixtures of any number of materials, or in layered compositions of materials. In addition, solid cores can be composed of a polymeric core such as amphiphilic block copolymers, hydrophobic polymers such as polystyrene, poly(lactic acid), poly(lactic co-glycolic acid), poly(glycolic acid), poly(caprolactone) and other biocompatible polymers known to those skilled in the art.

The core may alternatively be a hollow core, which has at least some space in the center region of a shell material. Hollow cores include liposomal cores. A liposomal core as used herein refers to a centrally located core compartment formed by a component of the lipids or phospholipids that form a lipid bilayer. "Liposomes" are artificial, self closed vesicular structure of various sizes and structures, where one or several membranes encapsulate an aqueous core. Most typically liposome membranes are formed from lipid bilayers membranes, where the hydrophilic head groups are oriented towards the aqueous environment and the lipid chains are embedded in the lipophilic core. Liposomes can be formed as well from other amphiphilic monomeric and polymeric molecules, such as polymers, like block copolymers, or polypeptides or lipid monolayers. Unilamellar vesicles are liposomes defined by a single membrane enclosing an aqueous space. In contrast, oligo- or multilamellar vesicles are built up of several membranes. Typically, the membranes are roughly 4 nm thick and are composed of amphiphilic lipids, such as phospholipids, of natural or synthetic origin. Optionally, the membrane properties can be modified by the incorporation of other lipids such as sterols or cholic acid derivatives.

A lipid bilayer is composed of two layers of lipid molecules and a lipid monolayer is composed of one layer of lipid molecules. Each lipid molecule in a layer is oriented substantially parallel to adjacent lipid bilayers, and two layers that form a bilayer have the polar ends of their molecules exposed to the aqueous phase and the non-polar ends adjacent to each other. The central aqueous region of the liposomal core may be empty or filled fully or partially with water, an aqueous emulsion, oligonucleotides, or other therapeutic or diagnostic agent.

"Lipid" is a generic term encompassing fats, lipids, alcohol-ether-soluble constituents of protoplasm, which are insoluble in water. Lipids usually consist of a hydrophilic and a hydrophobic moiety. In water lipids can self organize to form bilayers membranes, where the hydrophilic moieties (head groups) are oriented towards the aqueous phase, and the lipophilic moieties (acyl chains) are embedded in the bilayers core. Lipids can comprise as well two hydrophilic moieties (bola amphiphiles). In that case, membranes may be formed from a single lipid layer, and not a bilayer. Typical examples for lipids in the current context are fats, fatty oils, essential oils, waxes, steroid, sterols, phospholipids, glycolipids, sulpholipids, aminolipids, chromolipids, and fatty acids. The term encompasses both naturally occurring and synthetic lipids. Preferred lipids in connection with the present invention are: steroids and sterol, particularly cholesterol, phospholipids, including phosphatidyl, phosphatidylcholines and phosphatidylethanolamines and sphingomyelins. Where there are fatty acids, they could be about 12-24 carbon chains in length, containing up to 6 double bonds. The fatty acids are linked to the backbone, which may be derived from glycerol. The fatty acids within one lipid can be different (asymmetric), or there may be only 1 fatty acid chain present, e.g. lysolecithins. Mixed formulations are also possible, particularly when the non-cationic lipids are derived from natural sources, such as lecithins (phosphatidylcholines) purified from egg yolk, bovine heart, brain, liver or soybean.

The liposomal core can be constructed from one or more lipids known to those in the art including but not limited to: sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, and their derivatives.

The oligonucleotides are positioned on or coupled to the exterior of the lipidated structure. Coupled may be direct or indirect or reversible or irreversible. Reversibly coupled compounds are associated with one another using a susceptible linkage. A susceptible linkage is one which is susceptible to separation under physiological conditions. For instance Watson crick base pairing is a susceptible linkage. Cleavable linkers are also susceptible linkages.

A dense configuration of oligonucleotides is a collection of oligonucleotides situated in close proximity to one another. At least two oligonucleotides are positioned on the exterior of the lipidated structure. In some embodiments at least 25, 50, 75, 100, 200, 300, 400, 500, 600, 700, 800, 900, 1,000, 2,000, 3,000, 4,000, 5,000, 6,000, 7,000, 8,000, 9,000 or 10,000 oligonucleotides or any range combination thereof are on the exterior of the lipidated structure. In some embodiments, 1-1000, 2-10,000, 10-500, 50-250, 50-300, 1,000-10,000, 2,000-10,000, 3,000-10,000, 4,000-10,000, 5,000-10,000, 6,000-10,000, 7,000-10,000, 8,000-10,000, 9,000-10,000, or 9,500-10,000 oligonucleotides are present on the surface.

In some instances the inhibitory oligonucleotides form an oligonucleotide shell. An oligonucleotide shell is formed when at least 50% of the available surface area of the exterior surface of the lipidated structure includes an oligonucleotide. In some embodiments at least 60%, 70%, 80%, 90%, 95%, 96%, 97% 98% or 99% of the available surface area of the exterior surface of the lipidated structure includes an oligonucleotide.

The oligonucleotides of the oligonucleotide shell may be oriented in a variety of directions. In some embodiments the oligonucleotides are oriented radially outwards. The orientation of these oligonucleotides can be either 5' distal/3' terminal in relation to the core, or 3' distal/5' terminal in relation to the core. In one embodiment one or a multiplicity of different oligonucleotides are present on the same surface of a single SNA. In all cases, at least 1 oligonucleotide is present on the surface but up to 10,000 can be present.

The oligonucleotides may be linked to the core or to one another and/or to other molecules such an active agents either directly or indirectly through a linker. The oligonucleotides may be conjugated to a linker via the 5' end or the 3' end, e.g. [Sequence, 5'-3']-Linker or Linker-[Sequence, 5'-3']. Some or all of the oligonucleotides of the nanostructure may be linked to one another either directly or indirectly through a covalent or non-covalent linkage. The linkage of one oligonucleotide to another oligonucleotide may be in addition to or alternatively to the linkage of that oligonucleotide to liposomal core. One or more of the oligonucleotides may also be linked to other molecules such as an alternative therapeutic agent. The oligonucleotides may be linked to the therapeutic either directly or indirectly through a covalent or non-covalent linkage.

The oligonucleotide shell formed of at least inhibitory oligonucleotide may be anchored to the surface of the lipidated structure or core through one or multiple of linker molecules, including but not limited to: any chemical structure containing one or multiple thiols, such as the various chain length alkane thiols, cyclic dithiol, lipoic acid, or other thiol linkers known to those skilled in the art.

In an embodiment containing a liposomal core, the oligonucleotide shell may be anchored to the surface of the liposomal core through conjugation to one or a multiplicity of linker molecules including but not limited to: tocopherols, sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, and their derivatives.

In some embodiments, PEG of different sizes is incorporated into the structure to alter the in vivo properties including but not limited to sizes from 1,000 Da to 40,000 Da.

The nanostructure may also include an active agent. An active agent as used herein is a molecule capable of providing some therapeutic or diagnostic advantage to a cell or subject. Active agents can be attached to the structures by the externally-facing oligonucleotides through covalent or non-covalent, e.g. Watson/Crick hybridization. Alternatively or additionally the active agents may be incorporated into a liposomal bilayer via conjugation to a hydrophobic moiety. In yet another embodiment, active agent may be incorporated inside the inner aqueous layer of the liposome.

In one embodiment, active agent is conjugated to the liposomal nanostructure via interactions with the oligonucleotide shell. In some instances the active agent—oligonucleotide conjugate is linked to the core through oligonucleotide hybridization. In other words the oligonucleotide is hybridized to a complementary or partially complementary oligonucleotide to form a duplex or partial duplex. One or both of the oligonucleotides of the duplex is linked directly to the core and the active agent which is external facing (on the outside of the lipid bilayer) or which is internal (in the inner aqueous layer) and not directly linked to the core is linked to one or both of the oligonucleotides in the duplex. In another embodiment, active agent is conjugated to the liposomal nanostructure via direct interactions with the core. The active agent can be anchored to the surface of the liposomal core through conjugation to one or a multiplicity of linker molecules including but not limited to: tocopherols, sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, and their derivatives.

The invention also encompasses the use of the inhibitory oligonucleotides for reducing gene expression in a cell. The method is achieved by contacting the cell with any of the inhibitory oligonucleotides or nanostructures described herein in order to reduce gene expression. For instance, a nanostructure comprising a nucleotide amphiphile having an inhibitory oligonucleotide having at least one GGG motif may be delivered to a cell to reduce gene expression A nucleotide amphiphile, as used herein, is a supramolecular structure comprised minimally of inhibitory oligonucleotides and lipids associated with one another through interactions including weak noncovalent chemical bonds. The lipids may be assembled into a liposomal structure which captures an end of the oligonucleotide. In some embodiments the nucleotide amphiphile is a spherical nucleic acid (SNA) as described herein.

The nucleotide amphiphile may be composed, in whole or in part, of nucleolipids. Nucleolipids possessing both nucleic acid components and lipophilic chains components are useful as building blocks for constructing these supramolecular structures because they include a diversity of functional groups capable of cooperative non-covalent interactions combined with specific base-base recognition. Nucleolipids may possess a polar head derived from either a purine base (adenine or guanine) or a pyrimidine base (cytosine, thymine or uracil). These bases can interact through π-stacking and hydrogen bonding, each base-base motif displaying different binding characteristics. The base pairs present in nucleic acids are adenine-thymine and guanine-cytosine in DNA double strands or adenine-uracil and guanine-cytosine in RNA double strands. Each strand of DNA (or RNA) is coupled through H-bonding to the other strand formed by the complementary bases sequence.

Gene expression may be reduced to a greater extent by when the cell is contacted with an inhibitory oligonucleotide in the form of a nanostructure than when the cell is contacted with free inhibitory oligonucleotide. The relative level of gene expression may be assessed using any methods known in the art. For instance, several methods are described herein. The skilled artisan is aware of other methods.

The inhibitory oligonucleotide is complementary to a target sequence. Numerous targets are available and known. In some embodiments the target is selected from the group consisting of TNF, Bcl-2, EGFR, mdm2, MyD88, PCSK9, survivin, VEGF, developmental genes (e.g. adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), oncogenes (e.g. ABLI, BLC1, BCL6, CBFA1, CBL, CSFIR, ERBA, ERBB, EBRB2, ETS1, ETS1, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES), tumor suppresser genes (e.g. APC, BRCA1, BRCA2, MADH4, MCC, NF1, NF2, RB1, TP53 and WT1), enzymes (e.g. ACP desaturases and hycroxylases, ADP-glucose pyrophorylases, ATPases, alcohol dehycrogenases, amylases, amyloglucosidases, catalases, cellulases, cyclooxygenases, decarboxylases, dextrinases, esterases, DNA and RNA polymerases, galactosidases, glucanases, glucose oxidases, GTPases, helicases, hemicellulases, integrases, invertases, isomersases, kinases, lactases, lipases, lipoxygenases, lysozymes, pectinesterases, peroxidases, phosphatases, phospholipases, phosphorylases, polygalacturonases, proteinases and peptideases, pullanases, recombinases, reverse transcriptases, topoisomerases, xylanases), and a TLR (e.g. TLR2, TLR3, TLR4, TLR5, TLR6, TLR7, TLR8 and TLR9). In some embodiments the inhibitory oligonucleotide is a therapeutic agent selected from the group consisting of anti-viral agents, anti-tumor agents, and agents for treating inherited disorders.

A nanostructure comprised of an inhibitory oligonucleotide may include multiple copies of the same oligonucleotide. Alternatively the structure may include multiple inhibitory oligonucleotides having different sequences. These different inhibitory oligonucleotides may be directed to the same or different targets, depending on the goal of the study or the therapy.

The invention also encompasses methods for the treatment of a subject having a condition or disease. The disorder may be, for instance, an autoimmune disease, an infectious disease, transplant rejection or graft-versus-host disease, malignancy, a pulmonary disorder, an intestinal disorder, a cardiac disorder, sepsis, a spondyloarthropathy, a metabolic disorder, anemia, pain, a hepatic disorder, a skin disorder, a nail disorder, rheumatoid arthritis, psoriasis, psoriasis in combination with psoriatic arthritis, ulcerative colitis, Crohn's disease, vasculitis, Behcet's disease, ankylosing spondylitis, asthma, chronic obstructive pulmonary disorder (COPD), idiopathic pulmonary fibrosis (IPF), restenosis, diabetes, anemia, pain, a Crohn's disease-related disorder, juvenile rheumatoid arthritis (JRA), a hepatitis C virus infection, psoriatic arthritis, and chronic plaque psoriasis.

The nanostructure can be combined with other unlinked therapeutic agents for treating the disorder. The nanostructure and/or other therapeutic agent may be administered simultaneously or sequentially. When the other therapeutic agents are administered simultaneously they can be administered in the same or separate formulations, but are administered at the same time. The other therapeutic agents are administered sequentially with one another and with the nanostructure, when the administration of the other therapeutic agents and the nanostructure and the therapeutic agent is temporally separated. The separation in time between the administration of these compounds may be a matter of minutes or it may be longer, e.g., days, weeks, months.

The term "effective amount" of an inhibitory oligonucleotide or a nanostructure containing the inhibitory oligonucleotide refers to the amount necessary or sufficient to realize a desired biologic effect. For example, an effective amount of an inhibitory oligonucleotide or a nanostructure containing the inhibitory oligonucleotide for treating or preventing disease is that amount necessary to prevent the progression or further worsening of the disease or is that amount necessary to decrease the amount severity or duration of the disease that would otherwise occur in the absence of the inhibitory oligonucleotide or a nanostructure containing the inhibitory oligonucleotide. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular nanostructure being administered the size of the subject, or the severity of the disease or condition. One of ordinary skill in the art can empirically determine the effective amount of a particular nanostructure without necessitating undue experimentation.

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 0.1 µg to 20 mg/kg/day, more typically from about 1 to 10 mg/kg/day, and most typically from about 1 to 5 mg/kg/day.

The inhibitory oligonucleotides or nanostructures containing the inhibitory oligonucleotides of the invention (referred to collectively as SNA) may be delivered to a subject in vivo or ex vivo for therapeutic and/or diagnostic use or may be used in vitro, ex vivo or in vivo for research purposes. The SNAs may be administered alone or in any appropriate pharmaceutical carrier, such as a liquid, for example saline, or a powder, for administration in vivo. They can also be co-delivered with larger carrier particles or within administration devices. The SNAs may be formulated or unformulated. The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients. In some embodiments, SNAs are mixed with a substance such as a lotion (for example, aquaphor) and are administered to the skin of a subject, whereby the SNAs are delivered through the skin of the subject. The SNAs may also be sterile.

In other embodiments of the invention, the SNA is administered on a routine schedule. A "routine schedule" as used herein, refers to a predetermined designated period of time. The routine schedule may encompass periods of time which are identical or which differ in length, as long as the schedule is predetermined. For instance, the routine schedule may involve administration of the SNA on a daily basis, every two days, every three days, every four days, every five days, every six days, a weekly basis, a monthly basis or any set number of days or weeks there-between, every two months, three months, four months, five months, six months, seven months, eight months, nine months, ten months, eleven months, twelve months, etc. Alternatively, the predetermined routine schedule may involve administration of the SNA on a daily basis for the first week, followed by a monthly basis for several months, and then every three months after that. Any particular combination would be covered by the routine schedule as long as it is determined ahead of time that the appropriate schedule involves administration on a certain day.

For use in therapy, an effective amount of the SNAs can be administered to a subject by any mode that delivers the SNAs to the desired cell. Administering pharmaceutical compositions may be accomplished by any means known to the skilled artisan. Routes of administration include but are not limited to oral, parenteral, intramuscular, intravenous, subcutaneous, mucosal, intranasal, sublingual, intratracheal, inhalation, ocular, vaginal, dermal, rectal, and by direct injection.

A subject shall mean a human or vertebrate animal including but not limited to a dog, cat, horse, cow, pig, sheep, goat, turkey, chicken, primate, e.g., monkey, and fish (aquaculture species), e.g. salmon. Thus, the invention can also be used to treat disease in non-human subjects.

As used herein, the term treat, treated, or treating when used with respect to an disorder refers to a prophylactic treatment which increases the resistance of a subject to development of the disease or, in other words, decreases the likelihood that the subject will develop the disease as well as a treatment after the subject has developed the disease in order to fight the disease or prevent the disease from becoming worse.

In another aspect, the present invention is directed to a kit including one or more of the compositions previously discussed. A "kit," as used herein, typically defines a package or an assembly including one or more of the compositions of the invention, and/or other compositions associated with the invention, for example, as previously described. Each of the compositions of the kit, if present, may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions that may be associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

In some embodiments, a kit associated with the invention includes one or more components of the SNA. For instance the kit may include liposomes for forming a liposome core or a metal for forming a solid core, and or inhibitory oligonucleotides for the exterior of the nanostructure. A kit can also include one or more other therapeutic agents.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the use of the compositions, for example, for a particular use, e.g., to a sample. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

In order that the invention described herein may be more fully understood, the following examples are set forth. The examples described in this application are offered to illustrate the compounds, pharmaceutical compositions, and methods provided herein and are not to be construed in any way as limiting their scope.

EXAMPLES

Example 1: Correlation of Sequence Features with Antisense SNA Potency

Methods

I. Liposomal Spherical Nucleic Acid Synthesis

Dioleoylphosphatidylcholine (DOPC) liposomes, approximately 50 nm in diameter, were synthesized via extrusion. Under RNAse-free and sterile conditions, the active and negative control antisense oligonucleotides were added liposomes and allowed to stand overnight. The lipids at the 3' end of the oligonucleotides insert into the DOPC bilayer, resulting in an external nucleic acid functionalization of liposome. These SNAs were functionalized with a final loading of 100 antisense strands per liposome. Liposomal SNAs have been found to incorporate nucleic acids essentially quantitatively. SNAs were stored at 4° C. until the day of transfection when they were warmed to room temperature prior to use.

II. Cell Culture and Transfections

Primary human fetal keratinocytes (HKFs) were maintained in Medium 154 (Life Technologies, M-154CF-500) supplemented with 70 µM calcium chloride and 1% human keratinocyte growth supplement (HKGS, Life Technologies, S-001-K). Primary neonatal human epidermal melanocytes (HEMn) were maintained in Medium 254 (Life Technologies, M-254-500) supplemented with 1% human melanocyte growth supplement (HMGS, Life Technologies, S-002-5). For HFK experiments, cells were seeded at passage 5 at a density of 15,000 cells per well in 96-well tissue culture treated plates. For HEMn experiments, cells were seeded between passages 7-12 in a similar manner to that of the HFKs. HFK cells were treated in quadruplicate with inhibitory SNAs targeting nuclear factor-kappa B1 (NF-κB1), interleukin-22 receptor A1 (IL-22RA1), interleukin-17 receptor A1 (IL-17RA1), or receptor for advanced glycation end-products (RAGE) and a non-targeting control SNA. In all experiments, the SNA concentration was 5 nM (the corresponding antisense concentration was 500 nM) in fresh maintenance media. HEMn cells were treated in quadruplicate with inhibitory SNAs targeting tyrosinase (TYR) and a non-targeting control SNA at a final SNA concentration of 5 nM (antisense concentration of 500 nM) in fresh maintenance media. The SNAs were incubated with the cells for 24 hours.

III. RNA Isolation and Real-Time PCR

Cells were lysed in RLT Buffer (Qiagen) after the 24 hr SNA transfection. RNA was isolated from lysates using the RNEasy 96-well kit (Qiagen) according to the manufacturer's instructions. cDNA was then synthesized from the RNA isolates using a cDNA high capacity reverse transcription kit (Life Technologies). RNA isolates were treated on a thermocycler at 25° C. for 10 minutes, 37° C. for 90 minutes, 85° C. for 5 minutes with a 4° C. hold to generate cDNA. RT-PCR was performed using a mixture containing 6 µL of the synthesized cDNA, 4.66 µL LightCycler480 probes master mix (Roche), 0.47 µL of gene specific FAM-labeled probes and primers, and 0.37 µL human glyceraldehyde-3-phosphate dehydrogenase (GAPDH) specific HEX-labeled probe and primers per reaction well of a 384-well optical reaction plate (Roche). The primer and probe sets for NF-κB1, IL22RA, IL17RA, RAGE, TYR and GAPDH were designed using the known human genome sequence (NCBI reference sequences NM_003998.3, NM_021258.3, NM_014339.6, NM_001136.4, NM_000372.4 and NM_002046.4, respectively) and were found to be specific by "blastn" analysis (NCBI). The oligonucleotide probes and primers used can be found in the table below. RT-PCR reactions, in duplicate, were carried out on the Roche Lightcycler 480 with the following cycle programming: initial denaturation at 95° C. for 10 minutes and then 50 cycles of denaturation at 95° C. for 10 seconds, annealing at 60° C. for 30 seconds and extension at 72° C. for 1 second. Cp values were obtained by analysis with the $2^{nd}$ derivative method. Relative gene expression was determined by normalization with the housekeeping gene (GAPDH) and the AA-Cp method. Each active SNA was compared to its control SNA.

| Gene/ Oligo- nucleo- tide Name | SEQ ID NO. | Sequence (5'->3') |
|---|---|---|
| NF-κB1 Forward Primer | 1 | ACTCTGGCGCAGAAATTAGG |
| NF-κB1 Reverse Primer | 2 | TGTAGCCCATTTGTCTCAGG |
| NF-κB1 Probe | 3 | /FAM/ACAACTATGAGGTCTCTGGGGGTAC/BHQ1/ |
| IL22RA Forward Primer | 4 | GCTGCTGACCATCTTGACTG |
| IL22RA Reverse Primer | 5 | GGACTGGAATTTCACGTGCTG |
| IL22RA Probe | 6 | /FAM/CTGAGGACCCCTCGGATCTGCT/BHQ1/ |
| IL17RA Forward Primer | 7 | AGAAATGCCAGACACTCCAG |
| IL17RA Reverse Primer | 8 | GATGGAGATGCCCGTGATG |
| IL17RA Probe | 9 | /FAM/CCAATTCCGGACTACATGCCCCT/BHQ1/ |
| RAGE Forward Primer | 10 | GTCATCTTGTGGCAAAGGC |

| Gene/Oligo-nucleotide Name | SEQ ID NO. | Sequence (5'->3') |
|---|---|---|
| RAGE Reverse Primer | 11 | TGATTCAGTTCTGCACGCTC |
| RAGE Probe | 12 | /FAM/CAACGCCGAGGAGAGGAGAGGAAGG/BHQ1/ |
| TYR Forward Primer | 13 | TCCTAACTTACTCAGCCCAGCATC |
| TYR Reverse Primer | 14 | TGGCTGTTGTACTCCTCCAATCG |
| TYR Probe | 15 | /FAM/TCTCCTCTTGGCAGATTGTCTGTAGCCGA/BHQ1/ |
| GAPDH Forward Primer | 16 | CAAGGTCATCCATGACAACTTTG |
| GAPDH Reverse Primer | 17 | GGGCCATCCACAGTCTTCT |
| GAPDH Probe | 18 | /HEX/ACCACAGTCCATGCCATCACTGCCA/BHQ1/ |

The SNA knockdown data were analyzed as a function of the following antisense strand features: G content, number of G doublets, triplets, and quadruplets, and strand self-dimerization AG (Table 1). In the analysis, the knockdown data against five different genes (Tables 2-6) were merged together.

Results

The presence of a GGG motif in the sequences of the dataset gives rise to a statistically significant increase in knockdown versus those sequences without the specific motif.

TABLE 1

Percent mRNA Expression after Treatment with 5 nM Hollow SNA

| Internal Code | SEQ ID NO. | Molecule | mRNA Target | #GGG | % mRNA Expression |
|---|---|---|---|---|---|
| Oligo 5003 | 19 | mAmGmGmUmGmGC*T*T*G*A*G*mGmGmUmAmGmU/iSp18//iSp18//Chol/ | IL22RA | 1 | 47.5 |
| Oligo 5303 | 20 | mAmGmGmUmGmGC*T*T*G*A*G*mGmGmUmAmGmU/iSp18//iSp18//Stearyl/ | IL22RA | 1 | 37.9 |
| Oligo 5383 | 21 | T*A*G*A*G*T*G*A*G*G*T*C*A*G*G*C*T*T*/isp18//isp18//Chol/ | Tyrosinase | 0 | 101.8 |
| Oligo 5389 | 22 | mUmUmAmGmAG*T*G*A*G*G*T*C*A*G*mGmCmUmUmU/isp18//isp18//Stearyl/ | Tyrosinase | 0 | 88.0 |
| Oligo 5390 | 23 | mGmUmUmCmCT*C*A*T*T*A*C*A*A*mAmUmAmGmC/isp18//isp18//Stearyl/ | Tyrosinase | 0 | 88.0 |
| Oligo 5390 | 24 | mG*mU*mU*mC*mC*T*C*A*T*T*A*C*A*A*mA*mU*mA*mG*mC*/isp18//isp18//Stearyl/ | Tyrosinase | 0 | 97.0 |
| Oligo 5391 | 25 | mCmUmGmAmGT*G*A*A*A*A*C*A*G*C*mAmAmGmAmC/isp18//isp18//Stearyl/ | Tyrosinase | 0 | 96.0 |
| Oligo 5392 | 26 | mCmUmCmUmGmCC*T*G*A*A*A*mGmCmUmGmGmC/isp18//isp18//Stearyl/ | Tyrosinase | 0 | 88.8 |
| Oligo 5393 | 27 | mU*mC*mA*mU*mG*G*T*T*T*C*A*G*G*A*mU*mU*mA*mC*mG*/isp18//isp18//Stearyl/ | Tyrosinase | 0 | 92.1 |

TABLE 1-continued

| Oligo 5394 | 28 | mG*mA*mG*mC*mA*C*T*G *G*C*A*G*G*T*C*mC*mU* mA*mU*mU*/isp18// isp18//Stearyl/ | Tyrosinase | 0 | 104.2 |
|---|---|---|---|---|---|
| Oligo 5395 | 29 | mU*mU*mC*mC*mU*mC*A *T*T*A*C*C*mA*mA*mA* mU*mA*mG*/isp18// isp18//Stearyl/ | Tyrosinase | 0 | 95.0 |
| Oligo 5397 | 30 | mG*mU*mG*mC*mU*mG*A *C*C*T*C*C*C*A*T*mG*m U*mA*mC*mU*mC*/iSp18// iSp18//Stearyl/ | Tyrosinase | 0 | 80.0 |
| Oligo 5399 | 31 | mA*mC*mA*mC*mA*mG*G *C*T*C*T*T*A*mG*mG*mG* mA*mA*mA*/iSp18// iSp18//Stearyl/ | Tyrosinase | 1 | 84.0 |
| Oligo 5400 | 32 | mCmAmUmGmGmUT*T*C* C*A*G*mGmAmUmUmAmC/ isp18//isp18//Stearyl/ | Tyrosinase | 0 | 77.0 |
| Oligo 5401 | 33 | mUmUmGmGmAmAG*A*A* G*G*C*mUmAmCmAmCmU/ isp18//isp18//Stearyl/ | Tyrosinase | 0 | 79.0 |
| Oligo 5402 | 34 | mCmCmUmCmUG*C*C*T*G *A*A*A*G*C*mUmGmGmC mC/isp18//isp18// Stearyl/ | Tyrosinase | 0 | 75.7 |
| Oligo 5403 | 35 | mGmGmCmUmGA*G*T*A*A *G*T*T*A*G*mGmAmUmU mU/isp18//isp18// Stearyl/ | Tyrosinase | 0 | 70.0 |
| Oligo 5417 | 36 | C*A*C*T*A*G*T*T*T*C*C* A*A*G*T*C*A*G*A*T*/ iSp18//iSp18//Stearyl/ | NFKB | 0 | 104.0 |
| Oligo 5418 | 37 | C*A*C*G*C*T*G*A*G*G*T *C*C*A*T*C*T*T*C*/ iSp18//iSp18//Stearyl/ | NFKB | 0 | 115.0 |
| Oligo 5419 | 38 | C*A*A*C*T*G*C*T*G*T*T* C*C*G*G*C*T*G*C*/ isp18//iSp18//Stearyl/ | RAGE | 0 | 85.7 |
| Oligo 5481 | 39 | C*C*A*C*G*C*T*G*A*G*G *T*C*C*A*T*C*T*C*C*/ iSp18//iSp18//Stearyl/ | NFKB | 0 | 108.0 |
| Oligo 5484 | 40 | T*G*C*C*A*G*G*T*G*G*C *G*A*C*C*G*T*G*/ iSp18//iSp18//Stearyl/ | NFKB | 0 | 76.6 |
| Oligo 5486 | 41 | A*A*C*T*G*C*T*G*T*T*C* C*G*G*C*T*G*C*/isp18// isp18//Stearyl/ | RAGE | 0 | 78.0 |
| Oligo 5487 | 42 | A*T*G*C*T*G*A*C*A*G*C *A*C*G*G*C*T*T*T*C*/ isp18//isp18//Stearyl/ | RAGE | 0 | 88.7 |
| Oligo 5488 | 43 | C*T*C*C*T*T*T*C*C*A*T* T*C*C*T*G*T*T*C*A*/ isp18//isp18//Stearyl/ | RAGE | 0 | 98.9 |
| Oligo 5489 | 44 | mC*mA*mC*mU*mA*G*T*T *T*C*C*A*A*G*T*mC*mA* mG*mA*mU*/iSp18// iSp18//Stearyl/ | NFKB | 0 | 103.0 |
| Oligo 5490 | 45 | mA*mU*mG*mC*mC*A*G* G*T*G*G*C*G*A*C*mC*m G*mU*mG*mA*/iSp18// iSp18//Stearyl/ | NFKB | 0 | 77.0 |

TABLE 1-continued

| Oligo 5491 | 46 | mA*mC*mU*mA*mG*mU*T*T*C*C*A*mG*mU*mC*mA*mG*mA*/iSp18//iSp18//Stearyl/ | NFKB | 0 | 86.0 |
|---|---|---|---|---|---|
| Oligo 5492 | 47 | mU*mG*mC*mC*mA*mG*G*T*G*C*G*mA*mC*mC*mG*mU*mG*/iSp18//iSp18//Stearyl/ | NFKB | 0 | 81.0 |
| Oligo 5493 | 48 | mC*mA*mA*mC*mU*mG*C*T*G*T*T*C*C*mG*mG*mC*mU*mG*mC*/iSp18//iSp18//Stearyl/ | RAGE | 0 | 49.0 |
| Oligo 5494 | 49 | A*T*G*C*C*A*G*G*T*G*G*C*G*A*C*C*G*T*G*A*/iSp18//iSp18//Stearyl/ | NFKB | 0 | 79.6 |
| Oligo 5495 | 50 | mC*mU*mG*mC*mU*mU*C*C*T*T*T*C*C*mA*mG*mG*mG*mU*mC*/isp18//isp18//Stearyl/ | RAGE | 1 | 62.5 |
| Oligo 5500 | 51 | mC*mU*mU*mC*mC*mC*T*C*C*A*G*mG*mU*mG*mC*mA*mU*/iSp18//iSp18//Stearyl/ | IL22RA | 0 | 152.4 |
| Oligo 5501 | 52 | mC*mC*mC*mA*mC*mU*G*C*A*C*A*G*mU*mC*mA*mG*mG*mG*/iSp18//iSp18//Stearyl/ | IL22RA | 1 | 99.9 |
| Oligo 5502 | 53 | mA*mG*mG*mC*mA*mG*T*T*G*C*C*C*mU*mG*mG*mC*mU*mG*/iSp18//iSp18//Stearyl/ | IL22RA | 0 | 101.5 |
| Oligo 5506 | 54 | T*C*C*T*G*C*A*G*A*G*A*A*A*G*G*C*C*A*C*C*/iSp18//iSp18//Stearyl/ | IL22RA | 0 | 86.0 |
| Oligo 5509 | 55 | C*T*T*C*C*C*T*C*C*A*A*G*G*T*G*C*A*T*/iSp18//iSp18//Stearyl/ | IL22RA | 0 | 111.3 |
| Oligo 5511 | 56 | A*G*G*C*T*A*T*G*C*C*G*C*T*G*T*G*A*/iSp18//iSp18//Stearyl/ | IL22RA | 0 | 83.4 |
| Oligo 5544 | 57 | mU*mA*mG*mG*mG*C*G*T*G*T*G*G*G*mU*mC*mU*mG*mU*/iSp18//iSp18//Stearyl/ | IL17RA | 2 | 65.4 |
| Oligo 5551 | 58 | mC*mU*mC*mA*mC*T*C*C*A*C*T*C*A*C*C*mU*mC*mC*mC*mA*/iSp18//iSp18//Stearyl/ | IL17RA | 0 | 99.5 |
| Oligo 5552 | 59 | mU*mG*mU*mC*mC*T*G*T*T*T*G*C*T*C*T*mC*mC*mU*mG*mU*/iSp18//iSp18//Stearyl/ | IL17RA | 0 | 79.8 |
| Oligo 5553 | 60 | mA*mG*mA*mC*mG*A*T*A*A*C*C*A*G*A*C*mC*mG*mC*mU*mG*/iSp18//Stearyl/iSp18// | IL17RA | 0 | 66.8 |
| Oligo 5554 | 61 | mU*mA*mA*mC*mU*C*T*G*C*A*C*C*C*T*C*mG*mA*mG*mG*mU*/iSp18//iSp18//Stearyl/ | IL17RA | 0 | 81.0 |
| Oligo 5559 | 62 | T*G*T*C*C*T*G*T*T*T*G*C*T*C*T*C*C*T*G*T*/iSp18//iSp18//Stearyl/ | IL17RA | 0 | 95.6 |

TABLE 1-continued

| Oligo 5562 | 63 | mU*mU*mG*mU*mC*A*T*C *A*C*T*T*T*T*G*mU*mC* mA*mC*mA*/iSp18// iSp18//Stearyl/ | NFKB | 0 | 71.6 |
|---|---|---|---|---|---|
| Oligo 5563 | 64 | mC*mC*mA*mC*mG*C*T*G *A*G*T*C*C*A*mU*mC* mU*mC*mC*/iSp18// iSp18//Stearyl/ | NFKB | 0 | 61.1 |
| Oligo 5571 | 65 | mU*mG*mU*mC*mU*mG*T *G*C*A*A*A*mU*mC*mC* mC*mC*mA*/iSp18// iSp18//Stearyl/ | IL22RA | 0 | 102.7 |
| Oligo 5610 | 66 | mUmAmGmGmC*G*T*G*T *G*T*G*G*mUmCmUmG mU/iSp18//iSp18// Stearyl/ | IL17RA | 2 | 54.9 |
| Oligo 5614 | 67 | mCmCmAmCmAT*A*G*T*A *G*G*T*G*C*mAmCmAmA mU/iSp18//iSp18// Stearyl/ | IL17RA | 0 | 89.7 |
| Oligo 5618 | 68 | mCmUmCmAmCT*C*C*A*C *T*C*A*C*C*mUmCmCmCm A/iSp18//iSp18// Stearyl/ | IL17RA | 0 | 83.0 |
| Oligo 5619 | 69 | mUmGmUmCmCT*G*T*T*T *G*C*T*C*T*mCmCmUmGm U/iSp18//iSp18// Stearyl/ | IL17RA | 0 | 84.5 |
| Oligo 5621 | 70 | mAmGmAmCmGA*T*A*A*C *C*A*G*A*C*mCmGmCmU mG/iSp18//iSp18// Stearyl/ | IL17RA | 0 | 73.9 |
| Oligo 5622 | 71 | mUmAmAmCmUC*T*G*C*A *C*C*C*T*C*mGmAmGmG mU/iSp18//iSp18// Stearyl/ | IL17RA | 0 | 62.1 |
| Oligo 5623 | 72 | mAmCmUmAmGmUT*T*C* C*A*A*mGmUmCmAmGmA/ iSp18//iSp18//Stearyl/ | NFKB | 0 | 71.4 |
| Oligo 5624 | 73 | mCmUmGmCmUmUC*C*T*T *C*C*mAmGmGmGmUmC/ isp18//isp18//Stearyl/ | RAGE | 1 | 49.4 |
| Oligo 5630 | 74 | mUmCmCmCmAC*T*G*C*A *C*A*G*T*C*mAmGmGmG mC/iSp18//iSp18// Stearyl/ | IL22RA | 1 | 73.3 |
| Oligo 5631 | 75 | mCmAmGmGmCA*G*T*T*G *C*C*C*T*G*mGmCmUmG mG/iSp18//iSp18// Stearyl/ | IL22RA | 0 | 75.7 |
| Oligo 5632 | 76 | mCmUmCmCmCT*T*G*G*C *C*T*C*T*A*mCmUmCmUm G/iSp18//iSp18// Stearyl/ | IL22RA | 0 | 96.5 |
| Oligo 5636 | 77 | mUmGmUmCmUmGT*G*C* A*A*A*mUmCmCmCmCmA/ iSp18//iSp18//Stearyl/ | IL22RA | 0 | 84.0 |
| Oligo 5638 | 78 | mAmGmGmCmAmGT*T*G* C*C*C*mUmGmGmCmUmG/ iSp18//iSp18//Stearyl/ | IL22RA | 0 | 95.5 |
| Oligo 5646 | 79 | A*G*G*C*A*G*T*T*G*C*C *C*T*G*G*C*T*G*/iSp18// iSp18//Stearyl/ | IL22RA | 0 | 87.3 |

TABLE 1-continued

| Oligo 5710 | 80 | mUmGmGmUmAA*T*G*G* G*T*A*G*A*T*mUmCmGm UmU/iSp18//iSp18// Stearyl/ | IL17RA | 1 | 88.7 |
| --- | --- | --- | --- | --- | --- |
| Oligo 5909 | 81 | mGmUmUmUmCmAC*C*A* C*C*C*mAmAmUmUmCmC/ iSp18//iSp18//Stearyl/ | Control | 0 | N/A |
| Oligo 5416 | 82 | mGmUmUmUmCmAC*C*A* C*C*C*mAmAmUmUmCmC/ iSp18//iSp18//Chol/ | Control | 0 | N/A | mN = 2' O-Methyl RNA
* = Phosphorothioate internucleotide linkage
iSp18 = hexa(ethylene glycol) phosphodiester
Stearyl = Octadecyl phosphodiester
(www.glenresearch.com/ProductFiles/10-1979.html)
Chol = cholesteryl tetra(ethylene glycol) (CLP-2795 from ChemGenese)

| Gene | RefSeq | Citation | Comments |
| --- | --- | --- | --- |
| IL22RA | NM_021258.3 | J. Biol. Chem. 275 (40), 31335-31339 (2000) | The protein encoded by this gene belongs to the class II cytokine receptor family, and has been shown to be a receptor for interleukin 22(IL22). It is implicated in a variety of inflammatory conditions, including psoriasis. |
| RAGE/ AGER | NM_001136.4 | J. Biol. Chem. 267 (21), 14998-15004 (1992) | The advanced glycosylation end product (AGE) receptor encoded by this gene is a member of the immunoglobulin superfamily of cell surface receptors. It is a multiligand receptor, and besides AGE, interacts with other molecules implicated in homeostasis, development, and inflammation, and certain diseases, such as diabetes and Alzheimer's disease. Many alternatively spliced transcript variants encoding different isoforms, as well as non-protein-coding variants, have been described for this gene. It is related to aging and skin care. |
| Tyrosinase | NM_000372.4 | Science 217 (4565), 1163-1165 (1982) | The enzyme encoded by this gene catalyzes the first 2 steps, and at least 1 subsequent step, in the conversion of tyrosine to melanin. The enzyme has both tyrosine hydroxylase and dopa oxidase catalytic activities, and requires copper for function. Mutations in this gene result in oculocutaneous albinism, and nonpathologic polymorphisms result in skin pigmentation variation. The human genome contains a pseudogene similar to the 3' half of this gene. |
| IL17RA | NM_014339.6 | Trends in Pharmacological Sciences 30 (2), 95-103 (2009) | Interleukin 17A (IL17A) is a pro-inflammatory cytokine secreted by activated T-lymphocytes. It is a potent inducer of the maturation of CD34-positive hematopoietic precursors into neutrophils. The protein encoded by this gene (interleukin 17A receptor; IL17RA) is a ubiquitous type I membrane glycoprotein that binds with low affinity to interleukin 17A. Interleukin 17A and its receptor play a pathogenic role in many inflammatory and |

TABLE 1-continued

| | | | |
|---|---|---|---|
| | | | autoimmune diseases such as rheumatoid arthritis. |
| NFκB1 | NM_003998.3 | Annu. Rev. Immunol. 14: 649-83 | NF-KB (nuclear factor kappa-light-chain-enhancer of activated B cells) is a protein complex that controls transcription of DNA. NF-KB is found in almost all animal cell types and is involved in cellular responses to stimuli such as stress, cytokines, free radicals, ultraviolet irradiation, oxidized LDL, and bacterial or viral antigens. NF-KB plays a key role in regulating the immune response to infection (K light chains are critical components of immunoglobulins). Incorrect regulation of NF-KB has been linked to cancer, inflammatory, and autoimmune diseases, septic shock, viral infection, and improper immune development. |

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A spherical nucleic acid (SNA) comprising, a dense configuration of oligonucleotides radially positioned around a core, wherein the oligonucleotides have a length of 8-200 nucleotides and include at least one GGG, wherein the oligonucleotides are antisense oligonucleotides, wherein the oligonucleotides comprise the following structure:

5' $X_1$GGG$X_2$ 3' wherein $X_1$ and $X_2$ are, independent of one another, any nucleotide;

wherein the core is a liposomal core that comprises a lipid bilayer,
wherein the oligonucleotides are single-stranded,
wherein the oligonucleotides are indirectly linked to the core through a linker,
wherein the oligonucleotides have an mRNA target, and wherein the mRNA target is interleukin-17 receptor A1 (IL17RA).

2. The SNA of claim 1, wherein $X_1$ is selected from the group consisting of G and A.

3. The SNA of claim 1, wherein 5' $X_1GGGX_2$ 3' is selected from the group consisting of GGGG, GGGT, AGGG and GGGC.

4. The SNA of claim 1, wherein the oligonucleotides include 2-5 GGG motifs.

5. The SNA of claim 1, wherein the liposomal core is comprised of one type of lipid.

6. The SNA of claim 1, wherein the liposomal core is comprised of 2-10 different lipids.

7. The SNA of claim 1, wherein the oligonucleotides are nucleolipids.

8. The SNA of claim 1, wherein the at least one GGG is positioned at the 5' end of the oligonucleotide within the first 10 nucleotides.

9. The SNA of claim 1, wherein the at least one GGG is positioned at the 3' end of the oligonucleotide within the 10 nucleotides at the 3' end.

10. The SNA of claim 1, wherein the at least one GGG is positioned in the center of the oligonucleotide.

11. The SNA of claim 1, wherein the oligonucleotides comprise a hexaethylene glycol.

12. The SNA of claim 1, wherein at least 25 to 200 oligonucleotides are on the exterior of the lipidated structure.

13. The SNA of claim 1, wherein at least 50 to 100 oligonucleotides are on the exterior of the lipidated structure.

14. The SNA of claim 5, wherein the lipid is dioleoylphosphatidylcholine (DOPC).

15. The SNA of claim 1, wherein the core is a hollow core.

16. The SNA of claim 1, wherein the linker comprises a cholesterol.

17. The SNA of claim 1, wherein the oligonucleotides are conjugated to the linker via the 3'-end.

18. The SNA of claim 1, wherein the linker comprises two hexatheylene glycol spacers and a lipid selected from the group consisting of a stearyl and a cholesterol.

19. The SNA of claim 1, wherein 30%-90% of the nucleotides in each of the oligonucleotides are modified.

20. The SNA of claim 19, wherein the modifications are 2-O-methyl modifications and phosphorothioate backbone modifications.

* * * * *